United States Patent [19]

Tauber et al.

[11] 4,093,419
[45] June 6, 1978

[54] DEVICE FOR IRRADIATING LIQUID AND PASTY SUBSTANCES

[75] Inventors: Manfred Tauber, Holm; Dieter Heuer, Uetersen, both of Germany

[73] Assignee: Licentia Patent-Verwaltungs-G.m.b.H., Germany

[21] Appl. No.: 732,893

[22] Filed: Oct. 15, 1976

[30] Foreign Application Priority Data

Oct. 22, 1975 Germany ............................. 2547261

[51] Int. Cl.² ...................... A61L 3/00; G01N 23/12
[52] U.S. Cl. ................................. 21/102 R; 21/54 A; 21/DIG. 2; 250/428; 250/433; 366/147; 366/300; 366/301; 426/240; 99/451
[58] Field of Search ............ 21/54 A, 102 R, DIG. 2; 250/428–438; 99/451; 259/6, 21, 104 (U.S. only); 159/7, 9 A, 11 R (U.S. only); 426/240

[56] References Cited

U.S. PATENT DOCUMENTS

| 2,429,217 | 10/1947 | Brasch ............................ 250/429 |
| 3,336,008 | 8/1967 | Zoethout ............................ 259/6 |
| 4,048,504 | 9/1977 | Bosshard ...................... 250/432 R |

FOREIGN PATENT DOCUMENTS

| 564,968 | 8/1975 | Switzerland ............................ 21/54 R |
| 564,969 | 8/1975 | Switzerland ............................ 21/54 R |

Primary Examiner—Morris O. Wolk
Assistant Examiner—Roger F. Phillips
Attorney, Agent, or Firm—McGlew and Tuttle

[57] ABSTRACT

The device for irradiating liquid and pasty substances with high energy electrons in order to pasteurize or sterilize the irradiated substances and to enrich them with one or more additives, comprises a pair of cylindrical circulation members rotatably mounted in said housing and having radially extending helical blades. The members are located in a housing which has the shape of a solid figure eight formed of two tubes connected together and the walls of the housing conform to the path of the movement of the radial tips of the blades with a close clearance. The housing has an inlet for the substances to be irradiated at one end, and an outlet at the other end of the housing which is located between the axes of the rotatable members. The top of the housing has an irradiation opening between the axes of the circulation members and an electron deflecting horn of an electron beam radiating means has an electron accelerator disposed over the irradiation opening for directing a sweeping electron beam thereover.

6 Claims, 2 Drawing Figures

DEVICE FOR IRRADIATING LIQUID AND PASTY SUBSTANCES

FIELD AND BACKGROUND OF THE INVENTION

This invention relates in general to irradiation devices and, in particular, to a new and useful device for irradiating liquid and pasty substances with high energy electrons in order to pasteurize or sterilize the irradiated substances and, at the same time, to enrich them with one or more additives, particularly with gases.

DESCRIPTION OF THE PRIOR ART

German Pat. No. 2,258,393 shows a known method of irradiating liquids, granulated material, pulverulent substances, and still flowable media having a more or less high viscosity, which are received in a hollow body, with high energy electrons. The hollow body is accommodated in a box serving as an accumulator tank for the product to be irradiated. Mechanical means are provided for effecting a flow of the product to be irradiated from the box along the inner or outer walls of the hollow body and of the irradiated product back into the box or an additional receptacle. A radiator disposed within or outside the hollow body irradiates the product during the flow thereof along the walls of the hollow body. In this method of the prior art and the equipment intended for carrying out the method, no enrichment of the irradiated products with one or more additives, particularly gases, is provided. Such an enrichment, however, increases the effectivity of the irradiation with high energy electrons (synergistic effect) and, in particular, makes it possible to substantially reduce the necessary irradiation dosage.

SUMMARY OF THE INVENTION

The present invention is directed to a device for irradiating liquid and pasty substances with high energy electrons ensuring, while utilizing the synergistic effect, that every particle of the treated substance is quite satisfactorily irradiated. The additives introduced have to be used not only for increasing the effectivity of the irradiation, but also for either preventing undesirable chemical reactions or for supporting desired chemical reactions of the irradiated substances.

In accordance with the invention, two circulation members, which are disposed in parallel to each other and rotate in opposite directions, are provided with helically arranged blades and are mounted for rotation in a closed irradiation case having walls which extend in the axial direction of the circulation members and conform to the circular paths followed by the external ends of the blades. The housing or irradiation case has the shape of a solid figure eight formed of two tubes connected to each other. The irradiation case is provided, on one of its ends, with an inlet for feeding the substance to be irradiated and, on its other end, with an outlet for discharging the irradiated substance, and is also provided with one or a plurality of inlets for introducing an additive or additives. On the housing top side, intermediate the axes of the circulation members, there is an irradiation aperture above which an electron deflecting horn of an electron accelerator is disposed through which an electron beam sweeping the irradiation aperture is directed.

According to a development of the invention, the blades of the circulation members are secured to hollow shafts. A tempering means for positively tempering the circulation members can be supplied into the hollow spaces of the hollow shafts. Due to the positive tempering, the advantageous possibility is given to change the phase of the substance prior to, during, or after the irradiation.

A further development of the invention provides that the irradiation aperture is covered with a window. This makes it possible to use the electron exit window of the electron deflecting horn as a window for the irradiation aperture. An additional suction device may also be provided.

According to another feature of the invention, the irradiation case or housing comprises an overflow gutter which is disposed near the irradiation aperture and communicates with the inlet for the substance to be irradiated.

One advantage of the invention is that during its passage through the irradiation case, the irradiated substance is continuously mixed with the additive or additives. Further, and also advantageously, every particle of the substance to be irradiated passes through zones which are located in the immediate vicinity of the irradiation aperture, so that an irradiation of the whole substance is ensured. Another advantage of the invention becomes evident, for example, in the pasturization of sewage sludge, where air is introduced into the sludge as an additive and the ozone containing used air of the irradiation tank is employed as an oxygen carrier. Another advantage is that due to the forced mixing of the irradiated substance, the radiation is utilized in a more effective manner.

Accordingly, it is an object of the invention to provide a device for irradiating liquid and pasty substances with high energy electrons in order to pasteurize or sterilize the irradiated substances and to enrich them with one or more additives and which comprises a housing with a pair of cylindrical circulation members rotatably mounted in the housing and having radially extending blades, with the housing being in the form of a solid figure eight formed of two tubes connected together, and having walls which conform to the peripheries of the blades during their movement, and which also has an inlet at one end for the substance to be irradiated and a discharge at the opposite end for the irradiated substances and with a plurality of openings intermediate its length for the addition of additives and which includes a top wall for the irradiation opening defined between the axes of the circulation members and which is located below an electron beam radiation means for directing a sweeping electron beam over the irradiation opening.

A further object of the invention is to provide an irradiation device which is simple in design, rugged in construction and economical to manufacture.

The various features of novelty which characterize the invention are pointed out with particularity in the claims annexed to and forming a part of this disclosure. For a better understanding of the invention, its operating advantages and specific objects attained by its uses, reference should be had to the accompanying drawing and descriptive matter in which there is illustrated a preferred embodiment of the invention.

DESCRIPTION OF THE PREFERRED EMBODIMENT

Figure 1:
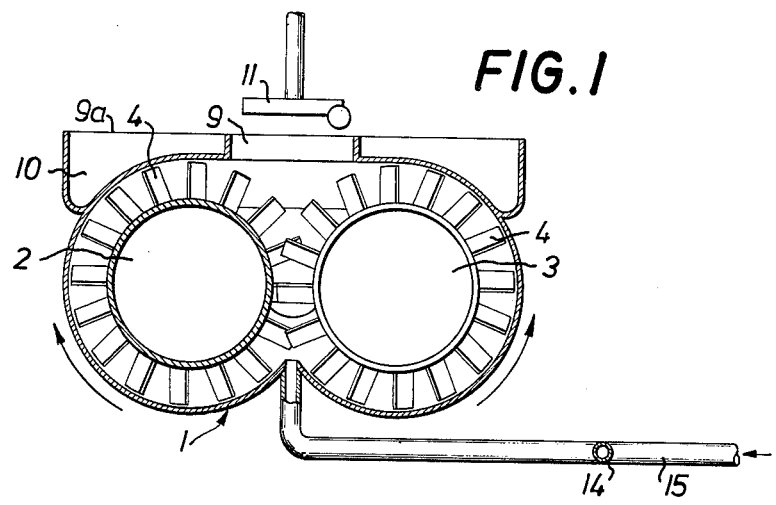
FIG. 1 is a transverse sectional view of an irradiation device constructed in accordance with the invention.

Referring to the drawings in particular, the invention embodied therein, comprises a irradiation device which includes an irradiation case or housing, generally designated 1, which is in the form of a solid figure eight being made up of two tubular portions which are arranged to overlap slightly and are interconnected. Two circulation members of cylindrical configuration 2 and 3, are disposed in parallel and are mounted for rotation in mutually opposite directions and carry a plurality of blades 4 which extend radially and are secured to the cylindrical members in a helical arrangement. The walls of casing 1 extend in the axial direction of circulation members 2 and 3 and they conform to the circular paths followed by the external ends of blades 4.

The front sides of the case 1 are closed by lateral sheets in which bearings 5, 5 are provided for shafts 4a and 4b of the circulation members 2 and 3. The end wall or end sheet also provides an inlet 6 for the substances to be irradiated and an outlet 7 for discharging the irradiated substances.

In the present example, the circulation members include two hollow shafts 8 which form carriers for the helically arranged blades 4 of the circulation members. However, solid shafts, for example, made of plastic may also be used. The use of the hollow shafts 8 make it possible to direct a tempering fluid into the hollow spaces to control the temperature of circulation members 2 and 3. It is then possible, if desired, to change the phase of the treated substance either in advance or during or after the irradiation.

The spacing of the external ends of blades 4 from the inner surface of irradiation case 1 must be relatively small in order to direct all the particles of the treated substances into the zone of the irradiation aperture 9 which is formed on a top wall 9a of casing or housing 1. Immediately adjacent the irradiation aperture 9 is an overflow gutter 10 which communicates with the inlet 6 for the substance to be irradiated. Above irradiation aperture 9, an electron deflecting horn 11 of an electron accelerator is mounted. This comprises an electron exit window through which the electron beam sweeps the irradiation aperture 9.

It is possible to cover irradiation aperture 9 of casing 1 by means of a window. For this purpose, the electron exit window of the electron deflecting horn, disposed directly over the irradiation aperture, may also be used. Should it be provided that these two component parts are spaced from each other by a predetermined distance, it is advantageous to connect the parts by a protective sheet surrounding irradiation aperture 9. In this case, the protective sheet and overflow gutter 10 may form an integral component part.

A piping system, generally designated 12, is provided for feeding in one or several additives and it comprises a plurality of parallel pipes 13. One end of each pipe 13 is connected to the interior of casing 1 while the other ends of pipes 13 are united by a common pipe 14 which is connected, through a supply pipe 15, to an injection or supply device, which has not been shown.

Figure 2:
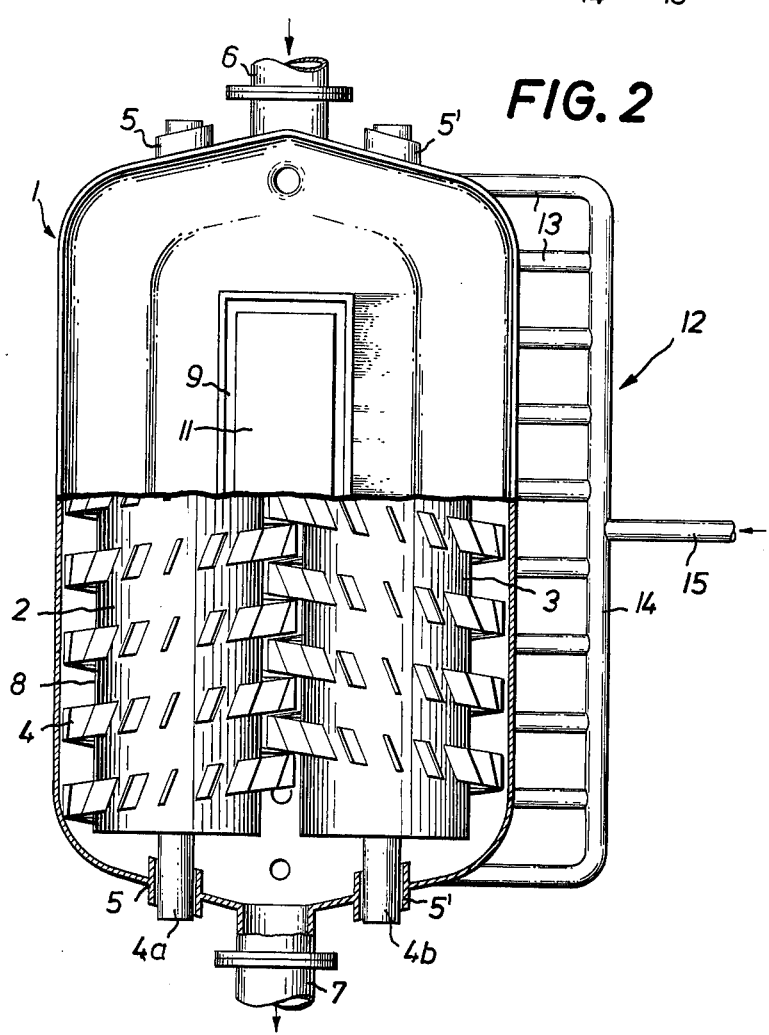
FIG. 2 is a horizontal sectional view of the irradiation device shown in FIG. 1.

The irradiation device in the embodiment shown in FIGS. 1 and 2 operates as follows:

The substance to be irradiated is pumped, through inlet 6, into irradiation casing 1 to which inlet 6 is mechanically firmly connected. Circulation members 2 and 3 which are mounted in irradiation case 1 rotate, in the direction of the arrows, shown in FIG. 1, in such a manner that the substance to be irradiated is continuously displaced along the inner surface of case 1 upwardly to irradiation aperture 9, that is, below deflecting horn 11 of the electron accelerator. This ensures that the treated substance is mixed well with the injected additive which is fed into case 1 through piping system 12. Due to the continuous feeding of the additive and the repeated irradiation of every particle of the additive, no disadvantageous effects in a pasteurization process of a possible impoverishment in oxygen due to the high density of energy of the electron beam can be expected. The irradiated substance is discharged through outlet 7 of case 1 and this outlet is advantageously connected to a storage tank or a device for further treatment.

While a specific embodiment of the invention has been shown and described in detail to illustrate the application of the principles of the invention, it will be understood that the invention may be embodied otherwise without departing from such principles.

What is claimed is:

1. A device for irradiating liquid and pasty substance with high energy electrons in order to pasteurize or sterilize the irradiated substances and to also enrich them with one or more additives, particularly with gases, comprising, a horizontally disposed housing, a pair of cylindrical circulation members rotatably mounted in said housing in parallel relationship and being rotatable in opposite directions and having radially extending helically arranged blades, said housing having walls which extend in the axial direction of said circulation members and are closely conformable to the annular paths followed by the peripheries of said blades during rotation thereof, said housing having the shape of a solid figure eight formed of two tubes connected together and having a front side with an inlet for feeding the substance to be irradiated and having an opposite rear side with an outlet for discharging the irradiated substances, said housing further being provided with a plurality of openings between said inlet and said outlet for the introduction of additives and having a top with an irradiation opening between the axes of said circulation members, and electron beam radiation means disposed over said irradiation opening for directing a sweeping electron beam over said irradiation opening.

2. A device for irradiating liquid and pasty substances, according to claim 1, wherein said electron beam radiation means comprises an electron deflecting horn of an electron accelerator, said circulation members including hollow shafts connected to said blades.

3. A device for irradiating liquid and pasty substances, according to claim 2, including means for supplying a temperature control means to said hollow shaft for tempering them.

4. A device for irradiating liquid and pasty substances, according to claim 1, including a window covering the irradiation aperture.

5. A device for irradiating liquid and pasty substances, according to claim 2, wherein said irradiation aperture is covered by a window, said electron deflecting horn having said window.

6. A device for irradiating liquid and pasty substances, according to claim 1, wherein said housing includes an overflow gutter adjacent the irradiation aperture and communicating with said inlet.

* * * * *